United States Patent
Iwamoto et al.

(10) Patent No.: US 6,344,592 B1
(45) Date of Patent: *Feb. 5, 2002

(54) METHOD OF PRODUCING HIGHLY PURE TRIMETHYLOLPROPANE

(75) Inventors: Atsushi Iwamoto; Teruyuki Ninomiya; Toshio Watanabe; Takaki Ikebe, all of Okayama (JP)

(73) Assignee: Mitsubishi Gas Chemical Company, Inc., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/467,212

(22) Filed: Dec. 20, 1999

(30) Foreign Application Priority Data

Dec. 25, 1998 (JP) .............................. 10-370418

(51) Int. Cl.⁷ ......................... C07C 31/18; C07C 27/26
(52) U.S. Cl. ..................... 568/853; 568/854; 568/869
(58) Field of Search ................................. 568/853, 854, 568/869

(56) References Cited

FOREIGN PATENT DOCUMENTS

GB    1290036    * 11/1970

* cited by examiner

*Primary Examiner*—Samuel Barts
*Assistant Examiner*—Elvis O. Prize
(74) *Attorney, Agent, or Firm*—Antonelli, Terry, Stout & Kraus, LLP

(57) ABSTRACT

A method of producing a highly pure trimethylolpropane from a crude trimethylolpropane obtained by a reaction of n-butyl aldehyde and formaldehyde in the presence of a basic catalyst in a two-stage process of an aldol condensation and a crossed Cannizzaro reaction. Since a high-boiling component and an inorganic salt are removed in advance from the crude trimethylolpropane, hardly removable impurities such as condensation products in the crude trimethylolpropane are changed in the subsequent heat treatment under acidic conditions to components easily removable by distillation. By distilling the heat-treated crude trimethylolpropane, a highly pure trimethylolpropane with a low content of remaining formaldehyde and a low coloring degree is easily obtained.

6 Claims, No Drawings

METHOD OF PRODUCING HIGHLY PURE TRIMETHYLOLPROPANE

BACKGROUND OF THE INVENTION

The present invention relates to a method of producing trimethylolpropane which is useful as a raw material for polyester resins, alkyd resins, polyurethane resins, polycarbonate resins, plasticizers, lubricating oils, surfactants, basis for cosmetics, reactive monomers, etc.

Trimethylolpropane (hereinafter referred to as "TMP") has been produced by a known two-stage process comprising an aldol condensation between n-butyl aldehyde (hereinafter referred to as "NBAL) and formaldehyde in the presence of a basic catalyst and a subsequent crossed Cannizzaro reaction between the aldol-condensation product and formaldehyde in a basic catalyst. For example, the two-stage process using sodium hydroxide is expressed by the following reaction scheme. (1) Aldol Condensation

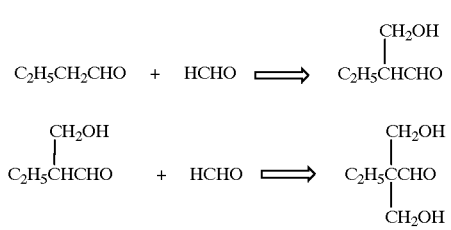

(2) Crossed Cannizzaro Reaction

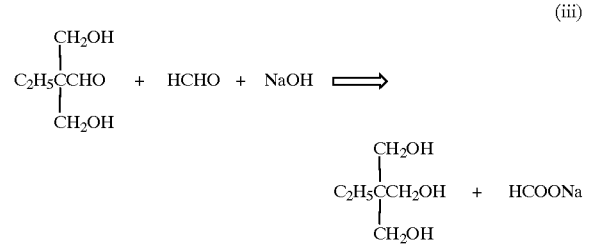

The liquid reaction mixture from the two-stage process contains a formic acid salt formed during the crossed Cannizzaro reaction. In the method known in the art, the liquid reaction mixture is distilled after removing most part of the formic acid salt by a solvent extraction or a hot filtration after condensing, and the resultant crude TMP distillate is rectified, thereby obtaining a final TMP with a high purity.

Japanese Patent Publication No. 50-9 discloses a method of purifying TMP, comprising a step of treating a crude TMP distillate under heating with a cation exchange resin in the presence of water and a subsequent step of vacuum-rectifying the treated crude TMP.

Recently, TMP has come into being widely used, and particularly in the use as a raw material for ultraviolet-curable resins, TMP having a purity higher than before has come to be required. However, since TMP after the solvent extraction, the hot filtration, etc. contains impurities which are hardly separated out by distillation, TMP with a high purity is difficult to obtain. The process proposed in Japanese Patent Publication No. 50-9 needs expensive cation exchange resins and requires troublesome operations, this making the process industrially unsuitable.

Therefore, an object of the present invention is to provide an industrially advantageous method of producing a highly pure TMP from a crude TMP obtained by a reaction between NBAL and formaldehyde in the presence of a basic catalyst in a two-stage process of an aldol condensation and a subsequent crossed Cannizzaro reaction.

SUMMARY OF THE INVENTION

As a result of extensive studies in the production method of TMP to eliminate the above problems, the inventors have found that a highly pure TMP is obtained from a crude TMP by removing in advance a high-boiling component and an inorganic salt such as sodium formate from the crude TMP, heat-treating the treated TMP under acidic conditions, and purifying the heat-treated TMP by distillation, etc. The present invention has been accomplished based on this finding.

Thus, the present invention provides a method of producing a highly pure trimethylolpropane, comprising the steps of removing a high-boiling component and an inorganic salt form a crude trimethylolpropane obtained by a reaction between n-butyl aldehyde and formaldehyde in the presence of a basic catalyst; heat-treating under acidic conditions the trimethylolpropane after removal of the high-boiling component and the inorganic salt; and purifying the heat-treated trimethylolpropane by distillation.

DETAILED DESCRIPTION OF THE INVENTION

The present invention relates to a purifying method of a crude TMP obtained by an aldol condensation and a subsequent crossed Cannizzaro reaction of NBAL and formaldehyde in the presence of a basic catalyst Formaldehyde used in the present invention as a starting material may be used in the form of aqueous solution or solid as paraformaldehyde. The molar ratio of formaldehyde to be used in the method with NBAL is 3.0 to 8.0 based on NBAL.

The basic catalyst for the aldol condensation and the crossed Cannizzaro reaction may include hydroxides of sodium, potassium, lithium and calcium; carbonates of these elements; hydrogencarbonates of these elements; and amines such as trimetylamine and triethylamine. These basic catalysts may be used alone or in combination of two or more. The salts of sodium or potassium are preferable for industrial process. The basic catalyst is used in an amount 1.0 to 2.0 times by mole of NBAL. To minimize by-production and increase the selectivity of the aimed TMP, it is preferred to adjust the amount of the basic catalyst according to the reaction conditions.

The first-stage aldol condensation and the second-stage crossed Cannizzaro reaction are usually successively carried out in the same reaction vessel without operationally distinguished from each other. The aldol condensation and the subsequent crossed Cannizzaro reaction may be carried out in the presence of water in an amount 2 to 20 times by weight of NBAL. After 0.2 to 3 hour reaction at 20 to 120° C. under reduced pressure, ordinary pressure or increased pressure, the reaction is completed.

The product mixture from the reaction of NBAL and formaldehyde is separated into, if necessary after removing the unreacted formaldehyde by condensation, the crude TMP and the formic acid salt by-produced during the crossed Cannizzaro reaction by a solvent extraction or a hot filtration after condensing. The solvent for the extraction may include ketones such as methyl ethyl ketone and methyl isobutyl ketone, aldehyde such as NBAL serving also as the starting material, alcohols such as isobutyl alcohol and isopropyl alcohol and esters such as butyl acetate, and usually used in a total amount of 0.2 to 10 times by weight of the product mixture. The solvent may be used alone or in combination of two or more. The hot filtration is carried out immediately after condensing the product mixture at 50 to 160° C. without cooling.

In the present invention, before the subsequent heat treatment, a high-boiling component and an inorganic salt including the remaining formic acid salt by-produced during the crossed Cannizzaro reaction are removed in advance from the crude TMP thus separated. The removal of the high-boiling component and the inorganic salt is preferably carried out by a thin-film distillation at 120 to 250° C. under a pressure of 0.01 to 20 Torr, because the treatment is finished in a short period of time. When the thin-film distillation is not applicable due to a high content of the remaining formic acid salt in the crude TMP, the inorganic acid and the high-boiling component are removed by distillation at 120 to 250° C. under a pressure of 0.01 to 20 Torr, after deactivating the formic acid salt by the addition of an acid such as phosphoric acid and sulfuric acid to avoid possible alkali pyrolysis of the formic acid salt. The deactivation is carried out by adding the acid to the crude TMP in an amount 0.2 to 2.0 times by mole of the formic acid salt, and then, heat-treating the resultant mixture at 120 to 250° C. for 0.5 to 3.0 hours under a pressure of 0.1 to 30 Torr.

After removal of the high-boiling component and the inorganic salt from the crude TMP, the resultant TMP distillate is heat-treated under acidic conditions. The TMP distillate is made acidic by adding an acid which shows pH 4 or less when made into 1% by weight aqueous solution. Such an acid may include mineral acids such as phosphoric acid and sulfuric acid and organic acids such as p-toluenesulfonic acid and methanesulfonic acid. Phosphoric acid and sulfuric acid are preferably used. Although depending on the heating conditions, the addition amount of the acid is usually from 10 ppm to 5% by weight, preferably 50 to 5000 ppm based on the TMP distillate. Impurities are hardly decomposed in an addition amount of less than 10 ppm, while TMP is likely to be colored or decomposed when the amount exceeds 5% by weight. The heat treatment is conducted at 140 to 200° C., preferably 160 to 180° C., for 10 to 300 minutes, preferably 50 to 150 minutes in air or inert gas atmosphere under ordinary pressure, increased pressure or reduced pressure.

TMP obtained by the reaction between NBAL and formaldehyde in the presence of the basic catalyst in the two-stage process of the aldol condensation and the subsequent crossed Cannizzaro reaction contains the impurities hardly removable by distillation. The impurities are free formaldehyde, condensation products of TMP and formaldehyde, methanol contained in the starting formalin, methanol formed during the crossed Cannizzaro reaction, condensation products of methanol, TMP and formaldehyde, etc. Specific examples for the condensation products are a cyclic monoformal (CMF) of the formula (I) derived from formaldehyde, a monomethylmonoformal (MMF) of the formula (II) and a monomethyldiformal (MDF) of the formula (III). In particular, MDF is impossible to separate from TMP by distillation because the relative volatility of MDF to TMP is nearly 1.

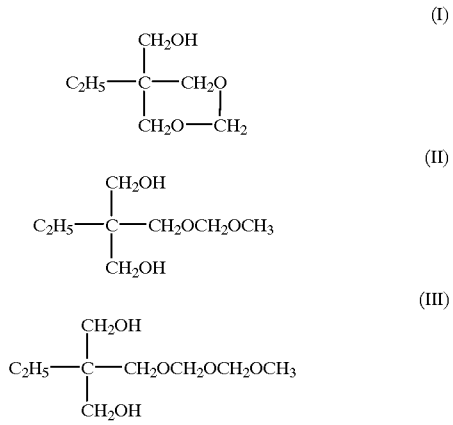

In addition, formaldehyde remaining in TMP product is not removed completely by a usual distillation. The quality of the final product is adversely affected by the remaining formaldehyde even in a small amount. To completely remove the impurities such as formaldehyde, MDF, etc. by distillation, much consideration should be given to the design of distillation column and complicated operating conditions are required, thereby making the removing process less economical. Thus, a highly pure TMP has not been obtained in the conventional distillation methods.

The condensation products mentioned above are known to be thermally decomposed under acidic conditions (Japanese Patent Publication No. 42-14605, etc.). However, when TMP contains the formic acid salt and the high-boiling component, the condensation products are hardly decomposed by the heat treatment in the presence of acid even in an amount equivalent to the amount of formic acid salt, thereby failing to obtain a highly pure TMP. Although the condensation products are decomposed by the heat treatment using excess amount of acid, a colored component, which is hardly removed from TMP by distillation, is formed from the high-boiling component.

In the present invention, as described above, after removing in advance the inorganic salt such as sodium formate and the high-boiling component from the crude TMP, the treated TMP is subjected to the heat treatment under acidic conditions. With such a heat treatment, the component hardly removable from TMP by distillation is thermally decomposed or chemically combined to: form a component readily removable from TMP by distillation.

For example, MMF and MDF each hardly removable by distillation are decomposed to CMF and methanol which are easily removable from TMP. Particularly, MDF quite difficult to remove by ordinary distillation is changed to easily removable components by the treatment of the invention, thereby enabling to obtain a highly pure TMP. In addition, since the remaining formaldehyde condenses with TMP to form easily removable CMF during the heat treatment under acidic conditions, a highly pure TMP is obtained.

The distillation of the heat-treated TMP may be carried out in any of the known manners, and is usually carried out at 120 to 250° C. under a pressure of 0.01 to 20 Torr. In the present invention, since the load of distillation column is reduced, the distillation apparatus is economically improved in respects of structure and operating manner, this enabling to produce a highly pure TMP advantageously in industrial scale.

The present invention will be explained in more detail by reference to the following examples which should not be construed to limit the scope of the present invention.

In the following examples and comparative examples, the content of the remaining formaldehyde in the final TMP product was determined by acetylacetone method, and the melt color was compared with APHA standard colors obtained according to JIS K 1557 6.2.

Preparation Example 1

An aqueous solution containing 4000 g of n-butyl aldehyde (NBAL), 13330 g of 40% formaldehyde aqueous solution and 2330 g of sodium hydroxide was heated at 50° C. for one hour under atmospheric pressure to allow NBAL to react with formaldehyde. After removing the unreacted formaldehyde, the reaction mixture was extracted by methyl ethyl ketone to obtain 7450 g of crude TMP containing 1.5% by weight of sodium formate, 7% by weight of low-boiling components and 7% by weight of high-boiling components.

EXAMPLE 1

After adding 45.2 g of phosphoric acid to 2000 g of the crude TMP obtained in Preparation Example 1, the resultant mixture was heated at 150° C. for one hour under a pressure of 50 Torr to deactivate sodium formate. The mixture thus treated was distilled at 180° C. under a pressure of 3 Torr to remove the inorganic salt such as sodium formate and the high-boiling components as the distillation residues while collecting TMP and the low-boiling components as the distillate. After adding 0.1 g of phosphoric acid to 1000 g of the distillate mainly comprising TMP, the mixture was heat-treated at 180° C in air for one hour under atmospheric pressure. The heat-treated distillate was purified by distillation at 150° C. under a reduced pressure of 1 Torr using a Sulzer-packed column of 10-theoretical stages. The gas chromatographic analysis showed that the purity of TMP obtained was 99.9%. The content of the remaining formaldehyde in the final TMP was 1 ppm.

Comparative Example 1

After adding 45.2 g of phosphoric acid to 2000 g of the crude TMP obtained in Preparation Example 1, the resultant mixture was heated at 150° C. for one hour under a pressure of 50 Torr to deactivate sodium formate. The mixture thus treated was distilled at 180° C. under a pressure of 3 Torr to remove the inorganic salt such as sodium formate and the high-boiling components as the distillation residues while collecting TMP and the low-boiling components as the distillate. Without adding phosphoric acid and subjecting to the heat treatment, 1000 g of the distillate mainly comprising TMP were purified by distillation at 150° C. under a reduced pressure of 1 Torr using a Sulzer-packed column of 10-theoretical stages. The purity of TMP obtained was 98.8%. The content of the remaining formaldehyde in the final TMP was 30 ppm.

Comparative Example 2

After adding 45.2 g of phosphoric acid to 2000 g of the crude TMP obtained in Preparation Example 1, the resultant mixture was heated at 150° C. for one hour under a pressure of 50 Torr to deactivate sodium formate. Then, after further adding 45.2 g of phosphoric acid, the heat treatment was continued at 180° C. in air for one hour under atmospheric pressure. The crude TMP thus heat-treated was purified by distillation at 150° C. under a reduced pressure of 1 Torr using a Sulzer-packed column of 10-theoretical stages. The purity of TMP obtained was 99.5%. The content of the remaining formaldehyde in the final TMP was 3 ppm. However, the melt color of the final TMP was detrimentally as high as 150.

Preparation Example 2

An aqueous solution containing 4000 g of n-butyl aldehyde (NBAL), 13330 g of 40% formaldehyde aqueous solution and 3236 g of sodium hydroxide was heated at 50° C. for one hour under atmospheric pressure to allow to react NBAL with formaldehyde. After removing the unreacted formaldehyde, the reaction mixture was extracted by NBAL to obtain 7430 g of crude TMP containing 0.3% by weight of sodium formate, 7% by weight of low-boiling components and 7% by weight of high-boiling components.

EXAMPLE 2

By subjecting 2000 g of the crude TMP obtained in Preparation Example 2 to thin-film distillation at 180° C. under a pressure of 1 Torr, sodium formate and the high-boiling components were removed from the crude TMP as the distillation residues while collecting TMP and the low-boiling components as the distillate. After adding 0.1 g of phosphoric acid to 1000 g of the distillate mainly comprising TMP, the mixture was heat-treated at 150° C. for one hour under a pressure of 5 Torr. The heat-treated distillate was purified by distillation at 150° C. under a reduced pressure of 1 Torr using a Sulzer-packed column of 10-theoretical stages. The gas chromatographic analysis showed that the purity of TMP obtained was 99.9%. The content of the remaining formaldehyde in the final TMP was 1 ppm.

Comparative Example 3

By subjecting 2000 g of the crude TMP obtained in Preparation Example 2 to thin-film distillation at 180° C. under a pressure of 1 Torr, sodium formate and the high-boiling components were removed from the crude TMP as the distillation residues while collecting TMP and the low-boiling components as the distillate. Without adding phosphoric acid and subjecting to the heat treatment, 1000 g of the distillate mainly comprising TMP were purified by distillation at 150° C. under a reduced pressure of 1 Torr using a Sulzer-packed column of 10-theoretical stages. The gas chromatographic analysis showed that the purity of TMP obtained was 98.8%. The content of the remaining formaldehyde in the final TMP was 30 ppm.

Comparative Example 4

After adding 9.0 g of phosphoric acid to 2000 g of the crude TMP obtained in Preparation Example 2, the resultant mixture was heat-treated at 180° C. in air for one hour under atmospheric pressure. The mixture thus treated was purified by distillation at 150° C. under a reduced pressure of 1 Torr using a Sulzer-packed column of 10-theoretical stages. The gas chromatographic analysis showed that the purity of TMP obtained was 99.5%. The content of the remaining formaldehyde in the final TMP was 5 ppm. However, the melt color of the final TMP was detrimentally as high as 110.

TABLE 1

|  | Purity (wt. %) | Remaining formaldehyde (ppm) | Melt Color (APHA) |
| --- | --- | --- | --- |
| Example 1 | 99.9 | 1 | 10 |
| Example 2 | 99.9 | 1 | 10 |
| Comparative | 98.8 | 30 | 10 |

TABLE 1-continued

|  | Purity (wt. %) | Remaining formaldehyde (ppm) | Melt Color (APHA) |
|---|---|---|---|
| Example 1 Comparative Example 2 | 99.5 | 3 | 150 |
| Comparative Example 3 | 98.8 | 30 | 10 |
| Comparative Example 4 | 99.5 | 5 | 110 |

TMP obtained by purifying a crude TMP by the method of the present invention has a purity as high as 99.8% or more, a small content of the remaining formaldehyde as low as 10 ppm or less and a low coloring degree of 20 or less in terms of APHA.

In the present invention, no expensive cation exchange resin, etc. are needed to use and the distillation apparatus is economically improved in respects of structure and operating manners due to the reduced load of distillation column. Therefore, a highly pure TMP usable as a raw material for ultraviolet curable resins is produced advantageously in industrial scale.

What is claimed is:

1. A method of producing a highly pure trimethylolpropane, comprising the steps of:

removing a high-boiling component and an inorganic salt from a crude trimethylolpropane obtained by a reaction between n-butyl aldehyde and formaldehyde in the presence of a basic catalyst;

heat-treating under acidic conditions the crude trimethylolpropane after removal of the high-boiling component and the inorganic salt, wherein the acidic conditions are provided by adding an acid which has a pH of 4 or less when made into 1% by weight aqueous solution, and wherein the heat treatment is carried out at 140° to 280° C. for 5 to 300 minutes; and purifying the heat-treated trimethylolpropane by distillation.

2. The method of producing a highly pure trimethylolpropane according to claim 1, wherein the removal of the high-boiling component and the inorganic salt is carried out after deactivating sodium formate present in the crude trimethylolpropane.

3. The method of producing a highly pure trimethylolpropane according to claim 1, wherein the acidic conditions are achieved by said adding said acid to the crude trimethylolpropane after subjected to the removing step in an amount from 10 ppm to 5% by weight based on the crude trimethylolpropane after subjected to the removing step.

4. The method of producing a highly pure trimethylolpropane according to claim 1, wherein the heat treatment is carried out at 140° to 200° C. for 10 to 300 minutes.

5. The method of producing a highly pure trimethylolpropane according to claim 4, wherein the heat treatment is carried out at 160° to 180° C. for 50 to 150 minutes.

6. The method of producing a highly pure trimethylolpropane according to claim 1, wherein the high-boiling component and the inorganic salt are removed by distillation.

* * * * *